US011723627B2

(12) United States Patent
Kozai

(10) Patent No.: US 11,723,627 B2
(45) Date of Patent: Aug. 15, 2023

(54) ULTRASOUND IMAGING SYSTEM, OPERATING METHOD OF ULTRASOUND IMAGING SYSTEM, AND COMPUTER-READABLE RECORDING MEDIUM

(71) Applicant: OLYMPUS CORPORATION, Tokyo (JP)

(72) Inventor: Shigenori Kozai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 498 days.

(21) Appl. No.: 16/905,720

(22) Filed: Jun. 18, 2020

(65) Prior Publication Data

US 2020/0315581 A1 Oct. 8, 2020

Related U.S. Application Data

(63) Continuation of application No. PCT/JP2018/045565, filed on Dec. 11, 2018.

(30) Foreign Application Priority Data

Dec. 20, 2017 (JP) ................................ 2017-244256

(51) Int. Cl.
*A61B 8/00* (2006.01)
*A61B 8/14* (2006.01)
*A61B 8/08* (2006.01)

(52) U.S. Cl.
CPC ................ *A61B 8/463* (2013.01); *A61B 8/14* (2013.01); *A61B 8/5207* (2013.01)

(58) Field of Classification Search
CPC .......... A61B 8/463; A61B 8/14; A61B 8/5207
See application file for complete search history.

(56) References Cited

U.S. PATENT DOCUMENTS

2007/0220980 A1 9/2007 Tanaka

FOREIGN PATENT DOCUMENTS

JP H09-000527 A 1/1997
JP 2001-269336 A 10/2001
(Continued)

OTHER PUBLICATIONS

International Search Report dated Feb. 5, 2019 issued in PCT/JP2018/045565.

*Primary Examiner* — Dixomara Vargas
(74) *Attorney, Agent, or Firm* — Scully, Scott, Murphy & Presser, P.C.

(57) ABSTRACT

Provided is an ultrasound imaging system configured to generate data of an ultrasound image based on an echo signal received by each of a plurality of elements included in an ultrasound transducer that transmits and receives ultrasound. The ultrasound imaging system includes: a determining circuit configured to determine, using a signal corresponding to the echo signal received by each of the plurality of elements, whether each of the plurality of elements has a sensitivity decrease; a region specifying circuit configured to specify a region where sensitivity decreases in the ultrasound image, based on a contribution degree indicating a ratio of transmission intensity contributing to an ultrasound beam by an element that has been determined as having the sensitivity decrease by the determining circuit; and a sensitivity display circuit configured to generate data for displaying the region specified by the region specifying circuit.

13 Claims, 8 Drawing Sheets

(56) References Cited

FOREIGN PATENT DOCUMENTS

| | | | |
|---|---|---|---|
| JP | 2002-159492 | A | 6/2002 |
| JP | 2007-252529 | A | 10/2007 |
| JP | 2009-178262 | A | 8/2009 |
| JP | 2013-165880 | A | 8/2013 |

FIG.2

| | | ELEMENTS | | | | | TOTAL CONTRIBUTION DEGREE OF SENSITIVITY DECREASE ELEMENTS | DISPLAY COLOR |
|---|---|---|---|---|---|---|---|---|
| | | E1 | E2 | E3 | E4 | E5 | | |
| SENSITIVITY DECREASE | | ABSENT | PRES-ENT | PRES-ENT | ABSENT | ABSENT | | |
| ULTRA-SOUND BEAM | B1 | 75% | 25% | 0% | 0% | 0% | 25% | YELLOW |
| | B2 | 25% | 50% | 25% | 0% | 0% | 75% | RED |
| | B3 | 0% | 25% | 50% | 25% | 0% | 75% | RED |
| | B4 | 0% | 0% | 25% | 50% | 25% | 25% | YELLOW |
| | B5 | 0% | 0% | 0% | 25% | 75% | 0% | WHITE |

FIG.5

| D1 | | ELEMENTS | | | | | TOTAL CONTRIBUTION DEGREE OF SENSITIVITY DECREASE ELEMENTS | DISPLAY COLOR |
|---|---|---|---|---|---|---|---|---|
| | | E1 | E2 | E3 | E4 | E5 | | |
| | SENSITIVITY DECREASE | ABSENT | PRES-ENT | PRES-ENT | ABSENT | ABSENT | | |
| ULTRA-SOUND BEAM | B11 | 75% | 25% | 0% | 0% | 0% | 25% | YELLOW |
| | B21 | 25% | 50% | 25% | 0% | 0% | 75% | RED |
| | B31 | 0% | 25% | 50% | 25% | 0% | 75% | RED |
| | B41 | 0% | 0% | 25% | 50% | 25% | 25% | YELLOW |
| | B51 | 0% | 0% | 0% | 25% | 75% | 0% | WHITE |

FIG.6

| D2 | | ELEMENTS | | | | | TOTAL CONTRIBUTION DEGREE OF SENSITIVITY DECREASE ELEMENTS | DISPLAY COLOR |
|---|---|---|---|---|---|---|---|---|
| | | E1 | E2 | E3 | E4 | E5 | | |
| SENSITIVITY DECREASE | | ABSENT | PRES-ENT | PRES-ENT | ABSENT | ABSENT | | |
| ULTRA-SOUND BEAM | B12 | 70% | 20% | 10% | 0% | 0% | 30% | YELLOW |
| | B22 | 10% | 40% | 40% | 10% | 0% | 80% | RED |
| | B32 | 0% | 10% | 40% | 40% | 10% | 50% | YELLOW |
| | B42 | 0% | 10% | 40% | 40% | 10% | 50% | YELLOW |
| | B52 | 0% | 0% | 10% | 20% | 70% | 10% | WHITE |

FIG.7

| D3 | | ELEMENTS | | | | | TOTAL CONTRIBUTION DEGREE OF SENSITIVITY DECREASE ELEMENTS | DISPLAY COLOR |
|---|---|---|---|---|---|---|---|---|
| | | E1 | E2 | E3 | E4 | E5 | | |
| SENSITIVITY DECREASE | | ABSENT | PRES-ENT | PRES-ENT | ABSENT | ABSENT | | |
| ULTRA-SOUND BEAM | B13 | 68% | 18% | 9% | 5% | 0% | 27% | YELLOW |
| | B23 | 9% | 38% | 38% | 9% | 6% | 76% | RED |
| | B33 | 11% | 20% | 38% | 20% | 11% | 58% | YELLOW |
| | B43 | 6% | 9% | 38% | 38% | 9% | 47% | YELLOW |
| | B53 | 0% | 5% | 9% | 18% | 68% | 14% | WHITE |

ULTRASOUND IMAGING SYSTEM, OPERATING METHOD OF ULTRASOUND IMAGING SYSTEM, AND COMPUTER-READABLE RECORDING MEDIUM

CROSS-REFERENCE TO RELATED APPLICATION

This application is a continuation of PCT International Application No. PCT/JP2018/045565 filed on Dec. 11, 2018, which designates the United States, incorporated herein by reference, and which claims the benefit of priority from Japanese Patent Application No. 2017-244256, filed on Dec. 20, 2017, incorporated herein by reference.

BACKGROUND

1. Technical Field

The present disclosure relates to an ultrasound imaging system, an operating method of the ultrasound imaging system, and a computer-readable recording medium.

2. Related Art

In an ultrasound diagnosis system that performs diagnosis using an ultrasound probe, it has been requested to, every time the ultrasound probe is connected to an ultrasound imaging device, inform a state of an ultrasound transducer included in the ultrasound probe to a user.

In an ultrasound probe of an electron scanning type, a plurality of elements included in an ultrasound transducer is driven at a time to acquire data of a sound ray. Accordingly, even if a sensitivity decrease occurs in one element, influence on an image is small. It is difficult for a user determine the sensitivity decrease from viewing the image.

Under such a situation, for example, JP H9-527 A discloses a technique including a circuit that detects an abnormal state for each transmission and reception channel of an ultrasound probe, the technique determining possibility of diagnosis when the abnormal state is detected and displaying a determination result. In this technique, information concerning a channel in the abnormal state is displayed by characters and informed to a user.

JP 2009-178262 A discloses a technique for determining, based on a reception signal obtained from a predetermined vibrating element for evaluation of an ultrasound probe, whether a sensitivity characteristic of the vibrating element for evaluation is normal, generating, based on a result of the determination, characteristic distribution data indicating a distribution of sensitivity characteristics of a plurality of vibrating elements, and determining possibility of diagnosis. In this technique, a display unit displays a vibrating element determined as abnormal to be distinguishable from a normal vibrating element to thereby inform an abnormal part of the ultrasound probe to a user.

SUMMARY

In some embodiments, provided is an ultrasound imaging system configured to generate data of an ultrasound image based on an echo signal received by each of a plurality of elements included in an ultrasound transducer that transmits and receives ultrasound. The ultrasound imaging system includes: a determining circuit configured to determine, using a signal corresponding to the echo signal received by each of the plurality of elements, whether each of the plurality of elements has a sensitivity decrease; a region specifying circuit configured to specify a region where sensitivity decreases in the ultrasound image, based on a contribution degree indicating a ratio of transmission intensity contributing to an ultrasound beam by an element that has been determined as having the sensitivity decrease by the determining circuit; and a sensitivity display circuit configured to generate data for displaying the region specified by the region specifying circuit.

In some embodiments, provided is an operating method of an ultrasound imaging system configured to generate data of an ultrasound image based on an echo signal received by each of a plurality of elements included in an ultrasound transducer that transmits and receives ultrasound. The operating method of the ultrasound imaging system includes: determining, using a signal corresponding to the echo signal received by each of the plurality of elements, whether each of the elements plurality of has a sensitivity decrease; specifying a region where sensitivity decreases in the ultrasound image, based on a contribution degree indicating a ratio of transmission intensity contributing to an ultrasound beam by an element that has been determined as having the sensitivity decrease by the determining; and generating data for displaying the region specified in the specifying.

In some embodiments, provided is a non-transitory computer-readable recording medium with an executable program stored thereon. The program causes an ultrasound imaging system configured to generate data of an ultrasound image based on an echo signal received by each of a plurality of elements included in an ultrasound transducer that transmits and receives ultrasound, to execute: determining, using a signal corresponding to the echo signal received by each of the plurality of elements, whether each of the plurality of elements has a sensitivity decrease; specifying a region where sensitivity decreases in the ultrasound image, based on a contribution degree indicating a ratio of transmission intensity contributing to an ultrasound beam by an element that has been determined as having the sensitivity decrease by the determining; and generating data for displaying the region specified in the specifying.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a diagram for explaining an overview of processing performed by a sensitivity image generating unit of the ultrasound imaging device according to the first embodiment of the disclosure;

FIG. 5 is a diagram (No. 1) illustrating an overview of processing performed by a sensitivity image generating unit of an ultrasound imaging device according to a second embodiment of the disclosure;

FIG. 6 is a diagram (No. 2) illustrating the overview of the processing performed by the sensitivity image generating unit of the ultrasound imaging device according to the second embodiment of the disclosure;

FIG. 7 is a diagram (No. 3) illustrating the overview of the processing performed by the sensitivity image generating unit of the ultrasound imaging device according to the second embodiment of the disclosure.

DETAILED DESCRIPTION

Modes for carrying out the disclosure (hereinafter referred to as "embodiments") are explained below with reference to the accompanying drawings.

First Embodiment

Figure 1:
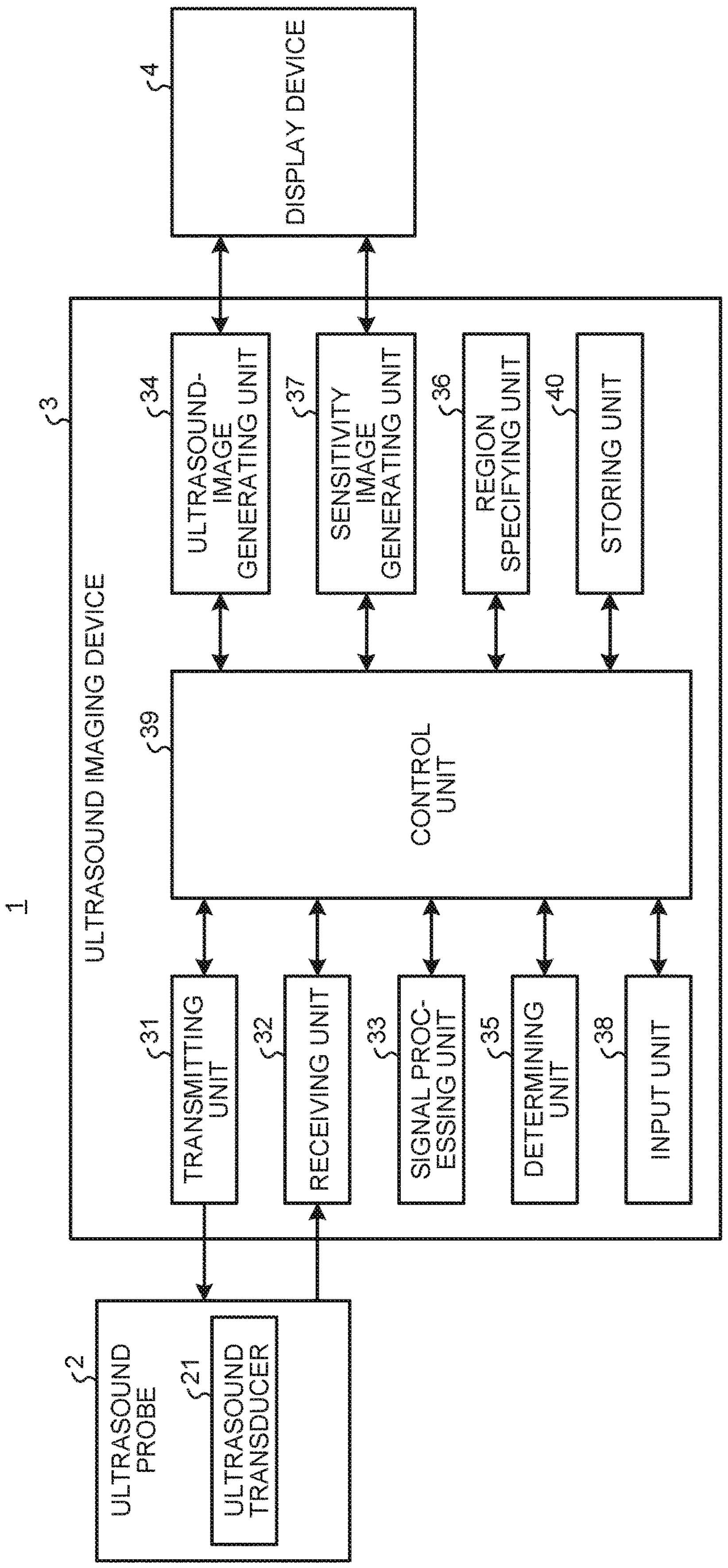
FIG. 1 is a block diagram illustrating a configuration of an ultrasound diagnosis system including an ultrasound imaging device according to a first embodiment of the disclosure.

FIG. 1 is a block diagram illustrating a configuration of an ultrasound diagnosis system including an ultrasound imaging device according to a first embodiment of the disclosure. An ultrasound diagnosis system 1 illustrated in the figure includes an ultrasound probe 2 that transmits ultrasound to a subject, which is an observation target, and receives the ultrasound reflected on the subject, an ultrasound imaging device 3 that generates an ultrasound image based on an ultrasound signal acquired by the ultrasound probe 2, and a display device 4 that displays the ultrasound image generated by the ultrasound imaging device 3.

The ultrasound probe 2 includes, at the distal end portion thereof, an ultrasound transducer 21 that converts an electric pulse signal received from the ultrasound imaging device 3 into an ultrasound pulse (an acoustic pulse) and irradiates the ultrasound pulse on the subject and converts an ultrasound echo reflected on the subject into an electric echo signal (an ultrasound signal) represented by a voltage change and outputs the echo signal. The ultrasound transducer 21 is an electron scanning type including a plurality of elements arranged in an array shape. The element is configured using a piezoelectric body of lead zirconate titanate (PZT), lead titanate (PT), lead niobate, or the like and performs conversion of mechanical energy and electric energy to thereby transmit and receive ultrasound. In the following explanation, the ultrasound transducer 21 of a radial type is explained. However, this is only an example. The ultrasound transducer 21 may be a convex type or a linear type.

The ultrasound probe 2 may be an ultrasound endoscope further including an imaging optical system and an imaging element or may be a thin miniature probe not including an optical system. The ultrasound probe 2 may be not only a type inserted into the body of a subject but also an external type that irradiates ultrasound from the body surface of a subject.

The ultrasound imaging device 3 includes a transmitting unit 31, a receiving unit 32, a signal processing unit 33, an ultrasound-image generating unit 34, a determining unit 35, a region specifying unit 36, a sensitivity image generating unit 37, an input unit 38, a control unit 39, and a storing unit 40.

The transmitting unit 31 is electrically connected to the ultrasound probe 2 and transmits a transmission signal (a pulse signal) to the ultrasound transducer 21. A frequency band of the pulse signal transmitted by the transmitting unit 31 is desirably set to a wideband that substantially covers a linear response frequency band of electroacoustic conversion of the pulse signal into an ultrasound pulse in the ultrasound transducer 21. The transmitting unit 31 transmits the transmission signal to a plurality of elements forming one sound ray while controlling transmission timings to the elements. The plurality of elements, which receives the transmission signal in this way, irradiates ultrasound beams. The transmitting unit 31 transmits various control signals output by the control unit 39 to the ultrasound probe 2. Note that power of a transmission signal transmitted by the transmitting unit 31 when presence or absence of a sensitivity decrease of an element is detected may be set higher compared with power of a transmission signal during an examination.

The receiving unit 32 receives an echo signal, which is an electric reception signal, from the ultrasound transducer 21 and A/D-converts the echo signal to thereby generate data of a digital radio frequency (RF) signal (hereinafter referred to as RF data). The receiving unit 32 also has a function of receiving various kinds of information including an ID for identification from the ultrasound probe 2 and transmitting the information to the control unit 39.

The signal processing unit 33 generates digital reception data for ultrasound image based on the RF data received from the receiving unit 32. Specifically, the signal processing unit 33 applies publicly-known processing such as digital beam forming (DBF) processing for adjusting and adding up phases of a plurality of RF data, envelope detection processing, and logarithmic conversion processing and generates digital reception data for ultrasound image. The reception data for ultrasound image includes a plurality of line data (sound ray data) in which amplitude or intensity of a reception signal indicating intensity of reflection of an ultrasound pulse is arranged along a transmission and reception direction (a depth direction) of the ultrasound pulse. The signal processing unit 33 outputs the generated reception data for ultrasound image for one frame to the ultrasound-image generating unit 34.

The ultrasound-image generating unit 34 generates ultrasound image data based on the reception data for ultrasound image received from the signal processing unit 33. The ultrasound-image generating unit 34 includes a digital scan converter (DSC) that converts the reception data for ultrasound image into data conforming to a display scheme of the display device 4. The ultrasound-image generating unit 34 further performs publicly-known signal processing such as gain processing and contrast processing to thereby generate ultrasound image data. The ultrasound image data is so-called B-mode image data. The B-mode image data is a gray scale image in which values of red (R), green (G), and blue (B), which are variables in the case in which an RGB color system is adopted as a color space, are matched.

The determining unit 35 analyzes the RF data received from the receiving unit 32 to thereby determine presence or absence of a sensitivity decrease in the elements included in the ultrasound transducer 21. The determining unit 35 detects the amplitude of the RF data as a sensitivity value and thereafter compares the sensitivity value with a predetermined threshold and determines an element having a sensitivity value smaller than the threshold as an element in which a sensitivity decrease is present (hereinafter referred to as sensitivity decreased element). The determining unit 35 writes, for example, sensitivity information setting the element determined as the sensitivity decreased element to 1 and setting the other elements to 0 in the storing unit 40 and causes the storing unit 40 to store the sensitivity information.

This determination processing is performed in a state in which the distal end portion of the ultrasound probe 2 is held in the air after a user connects the ultrasound probe 2 to the ultrasound imaging device 3. When the distal end portion of the ultrasound probe 2 is present in the air, the echo signal received by the receiving unit 32 in response to the transmission signal transmitted by the transmitting unit 31 is the echo signal reflected on the boundary surface between the ultrasound transducer 21 and the air and returned.

The region specifying unit 36 specifies, using sensitivity information for each of the elements stored by the storing unit 40, a region affected by a sensitivity decrease in the ultrasound image. The region specifying unit 36 specifies a sensitivity decreased part based on contribution degrees of elements equivalent to a transmission numerical aperture to ultrasound beams.

FIG. 2 is a diagram for explaining an overview of processing performed by the region specifying unit 36. FIG. 2 illustrates a case in which one ultrasound beam is formed using five elements E1 to E5 and illustrates a case in which the element E2 and the element E3 among the five elements E1 to E5 are determined as sensitivity decreased elements by the determining unit 35. It is assumed that the ultrasound probe 2 irradiates five ultrasound beams B1 to B5. It goes without saying that the number of elements included in the ultrasound transducer 21 is not limited to this. Each ultrasound beam Bi has the highest contribution degree of an element Ei, and has a lower contribution degree of an element that is more distant from the element Ei. For example, for the ultrasound beam B1, a contribution degree of the element E1 is 75%, a contribution degree of the element E2 is 25%, and contribution degrees of the elements E3 to E5 are respectively 0%. For the ultrasound beam B2, a contribution degree of the element E2 is 50%, contribution degrees of the elements E1 and E3 are respectively 25%, and contribution degrees of the elements E4 and E5 are respectively 0%. Information concerning the contribution degree to the ultrasound beam for each of the elements is stored in the storing unit 40.

Note that, in the above explanation, weighting corresponding to the contribution degree to the ultrasound beam is performed. However, the weighting may be performed by another method based on the contribution degrees of the elements to the ultrasound beam. For example, in FIG. 2, weights of the element Ei in the center and three elements adjacent to this element Ei among the elements forming the ultrasound beam Bi may be equally set to the maximum and weights of the other elements may be set relatively low. If the weight of at least the element in the center is the maximum and the weight of the element most distant from the element in the center is the minimum in this way, a weighting method is not limited to the method explained above.

The region specifying unit 36 calculates a total contribution degree obtained by totaling contribution degrees to each ultrasound beam for sensitivity decreased elements. A contribution degree is a contribution state (a ratio of contributing transmission intensity) to the ultrasound beam for each element. A sum of contribution degrees to one ultrasound beam is always 100%. A value obtained by totaling contribution degrees of sensitivity decreased elements among the contribution degrees is a value of the total contribution degree illustrated in the table. As this value is larger, the influence of the sensitivity decreased elements is larger. In the case illustrated in FIG. 2, contribution degrees of the sensitivity decreased elements E2 and E3 are respectively calculated for the ultrasound beams B1 to B5. A calculation result indicates that a total contribution degree to the ultrasound beam B1 is 25(%)+0(%)=25(%), a total contribution degree to the ultrasound beam B2 is 50(%)+25(%)=75(%), a total contribution degree to the ultrasound beam B3 is 25(%)+50(%)=75(%), a total contribution degree to the ultrasound beam B4 is 0(%)+25(%)=25(%), and a total contribution degree to the ultrasound beam B5 is 0(%)+0(%)=0(%).

The sensitivity image generating unit 37 generates data of a sensitivity image that displays a region (a sensitivity decreased part) specified by the region specifying unit 36. The sensitivity image generating unit 37 generates the data of the sensitivity image based on the total contribution degree calculated by the region specifying unit 36. In this case, the sensitivity image generating unit 37 allocates, for each of regions of an ultrasound image generated by the ultrasound beams, colors corresponding to the total contribution degree and generates data of a sensitivity image that displays sensitivity information of the region. For example, the sensitivity image generating unit 37 allocates “white” when the total contribution degree is 0% or more and 25% or less, allocates “yellow” when the total contribution degree is 25% more and less than 60%, and allocates “red” when the total contribution degree is 60% or more.

Figure 3:
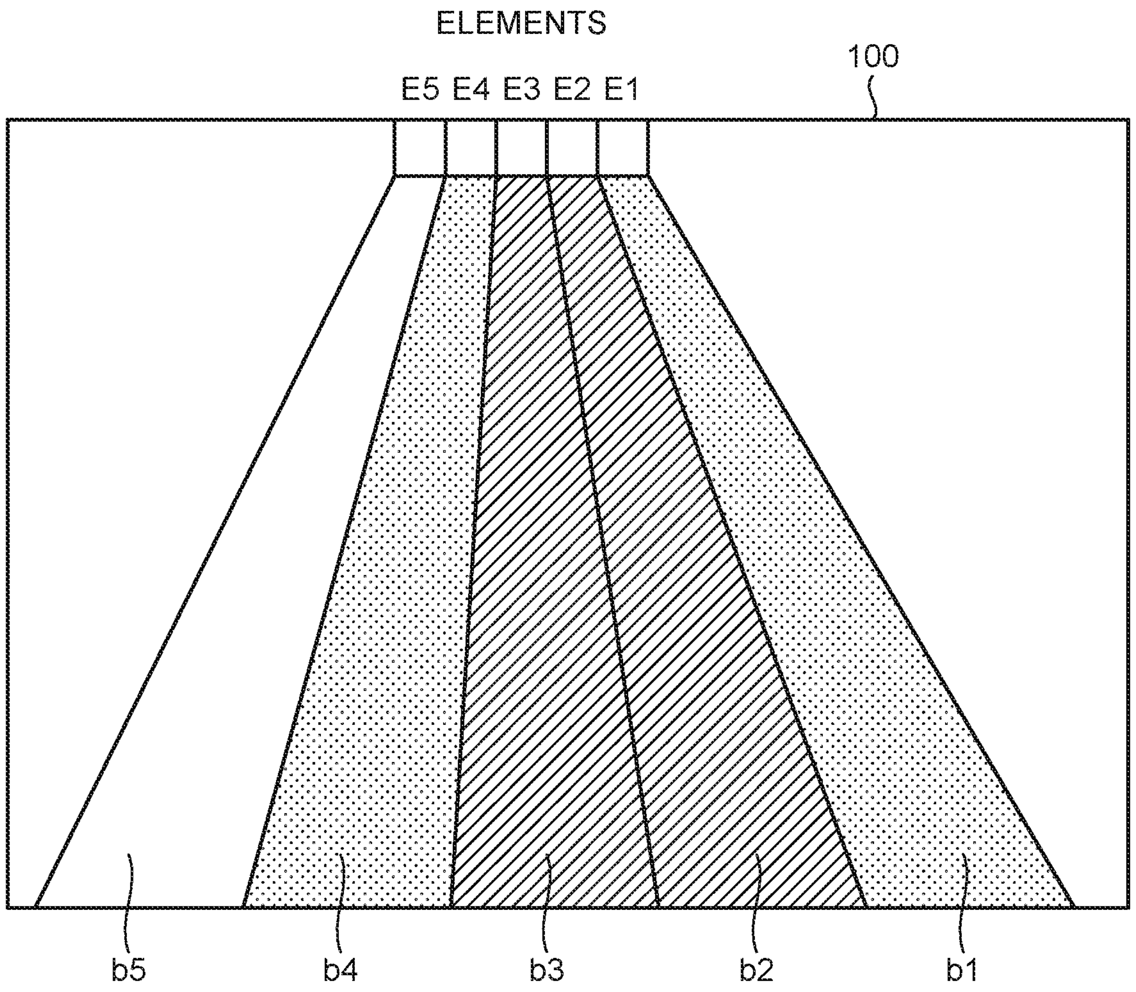
FIG. 3 is a diagram illustrating a display example of a sensitivity image displayed by a display device in the first embodiment of the disclosure.

FIG. 3 is a diagram illustrating a display example of a sensitivity image displayed by the display device 4. A sensitivity image 100 illustrated in the figure depicts a display example in the case in which the processing explained with reference to FIG. 2 is performed and the colors are allocated according to the rule explained above. The sensitivity image 100 displays, in yellow (in FIG. 3, dots), beam regions b1 and b4 respectively corresponding to the ultrasound beams B1 and B4, displays, in red (in FIG. 3, slant lines), beam regions b2 and b3 respectively corresponding to the ultrasound beams B2 and B3, and displays, in white, a beam region b5 corresponding to the ultrasound beam B5. Note that the sensitivity image generating unit 37 may generate the data of the sensitivity image by allocating visual information such as chroma, brightness, a design, or a pattern according to the total contribution degrees instead of allocating the colors corresponding to the total contribution degrees.

The input unit 38 is configured using a user interface such as a keyboard, a button, a mouse, a trackball, a touch panel, or a touch pad and receives inputs of various operation signals. As one of the various operation signals, a signal for instructing a start of sensitivity determination processing for the elements of the ultrasound transducer 21 is included.

The control unit 39 reads out information stored by the storing unit 40 from the storing unit 40 and executes various kinds of arithmetic processing relating to an operating method of the ultrasound imaging device 3 to thereby collectively control the operation of the ultrasound diagnosis system 1 including the ultrasound imaging device 3.

The storing unit 40 stores information such as a threshold of a sensitivity value referred to in the determination by the determining unit 35 and a result of determination for each of the elements by the determining unit 35, a relation between the ultrasound beam and the contribution degree of the element, the relation being referred to by the sensitivity image generating unit 37, a relation between the total contribution degree and the allocation of the color to the sensitivity image, and the like. The threshold of the sensitivity value stored by the storing unit 40 may be different depending on a type of the ultrasound probe 2. The storing unit 40 stores various programs for operating the ultrasound diagnosis system 1, data including various parameters necessary for the operation of the ultrasound diagnosis system 1, and the like. The various programs include an operating program for executing the operating method of the ultrasound diagnosis system 1. The various programs can also be widely distributed while being stored in a computer-readable storage medium such as a hard disk, a flash memory, a CD-ROM, a DVD-ROM, or a flexible disk. The various programs can also be acquired by being downloaded via a communication network. The communication network referred to herein is realized by, for example, an existing public line network, a local area network (LAN), or a wide area network (WAN) and may be either wired or wireless.

The ultrasound imaging device 3 having the configuration explained above is realized using a general-purpose processor such as a central processing unit (CPU) or a dedicated integrated circuit or the like that executes a specific function such as an application specific integrated circuit (ASIC) or a field programmable gate array (FPGA), a read only memory (ROM) in which various programs and the like are installed in advance, and a random access memory (RAM) or the like that stores operation parameters, data, and the like for respective kinds of processing.

The display device 4 receives data signals of the ultrasound image and the sensitivity image generated by the ultrasound imaging device 3 via a video cable and displays the data signals. The display device 4 is configured using a monitor of liquid crystal, organic electro luminescence (EL), or the like.

Figure 4:
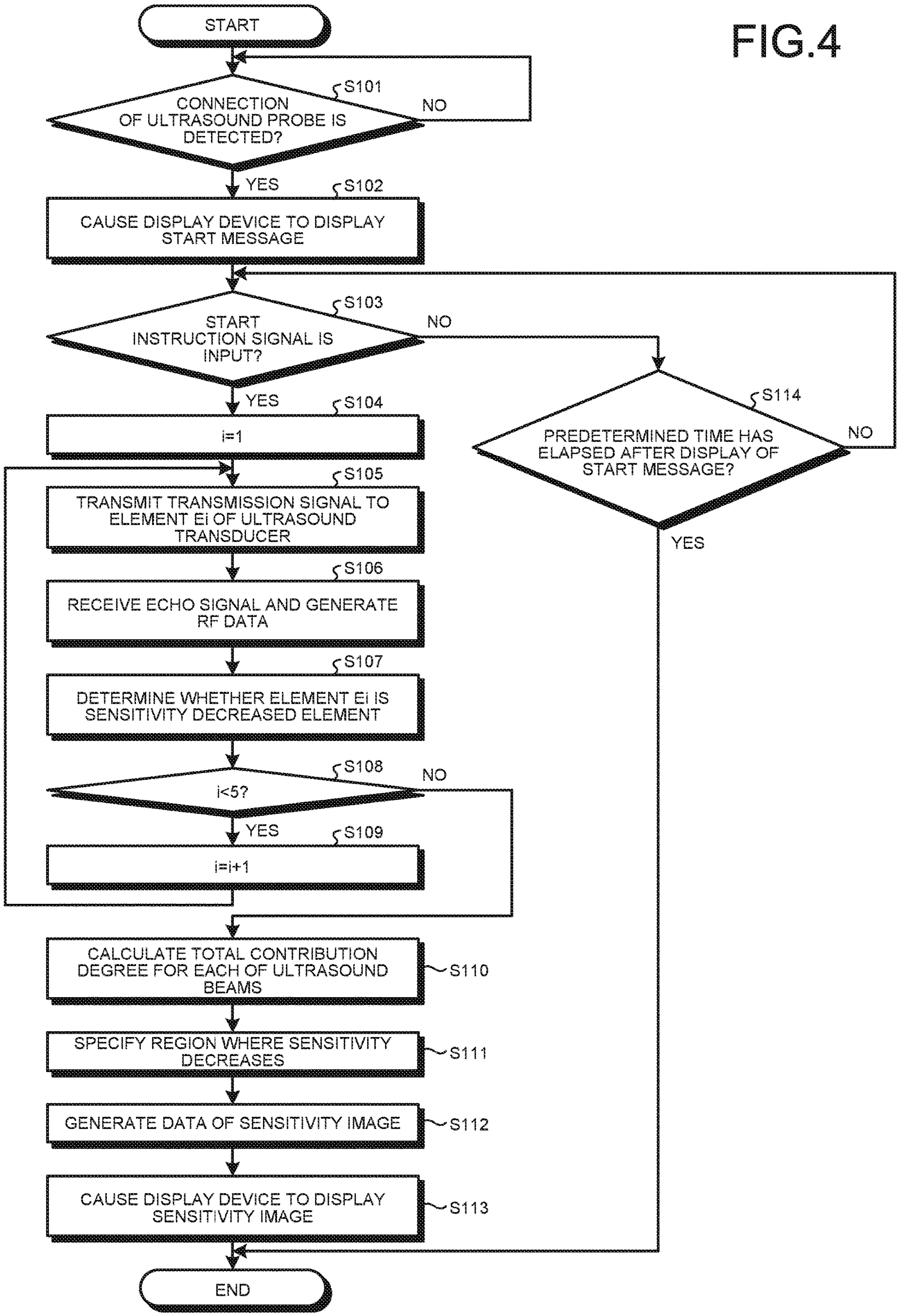
FIG. 4 is a flowchart illustrating an overview of element sensitivity determination processing performed by the ultrasound imaging device according to the first embodiment of the disclosure.

FIG. 4 is a flowchart illustrating an overview of element sensitivity determination processing performed by the ultrasound imaging device 3 having the configuration explained above. In the flowchart explained below, it is assumed that a power supply of the ultrasound imaging device 3 is in a turned-on state.

When the ultrasound probe 2 is connected to a connector of the ultrasound imaging device 3, the receiving unit 32 receives a signal from the ultrasound probe 2, and the control unit 39 detects the connection of the ultrasound probe 2 (step S101: Yes), the control unit 39 causes the display device 4 to display a start message for the element sensitivity determination processing (step S102). This start message has, for example, content "Start the element sensitivity determination processing for the elements of the ultrasound probe. Please press an OK button in a state in which the distal end portion of the ultrasound probe is kept in the air". When the control unit 39 does not detect the connection of the ultrasound probe 2 (step S101: No), the ultrasound imaging device 3 repeats step S101.

Thereafter, when the input unit 38 receives an input of a start instruction signal (step S103: Yes), the control unit 39 sets a counter i to an initial value 1 (step S104). Subsequently, the transmitting unit 31 selects the element Ei among the plurality of elements included in the ultrasound transducer 21 and transmits a transmission signal to the element Ei (step S105). Note that, in the above explanation, when the input unit 38 receives the input of the start instruction signal, the transmitting unit 31 transmits the transmission signal to the element E1. However, the transmitting unit 31 may automatically start to transmit the transmission signal to the element E1 when the control unit 39 detects the connection of the ultrasound probe 2.

Subsequently, the receiving unit 32 receives an echo signal from the ultrasound transducer 21, A/D-converts the echo signal to thereby generate RF data, and outputs the RF data to the determining unit 35 (step S106).

The determining unit 35 determines, using the RF data received from the receiving unit 32, whether the element Ei is a sensitivity decreased element and causes the storing unit 40 to store a determination result (step S107). The determining unit 35 calculates a sensitivity value of the element Ei from the RF data and, when the sensitivity value is lower than a threshold, determines the element Ei as the sensitivity decreased element. In the case illustrated in FIG. 2, the determining unit 35 determines the two elements E2 and E3 as sensitivity decreased elements.

Thereafter, the control unit 39 determines whether the counter i is smaller than the number 5 of elements (step S108). When the counter i is smaller than 5 (step S108: Yes), since the determination processing for all the elements has not ended, the control unit 39 increases the counter i by 1 (step S109) and performs control for returning to step S105. On the other hand, when the counter i is not smaller than 5 (step S108: No), since the determination processing for all the elements has ended, the control unit 39 performs control for shifting to step S110. When all the determination processing for all the elements by the determining unit 35 ends, for example, the information illustrated in FIG. 2 is stored in the storing unit 40.

Processing in step S110 and subsequent steps is explained. The region specifying unit 36 refers to the storing unit 40 and calculates a total contribution degree for each of ultrasound beams (step S110). A specific calculation method is as explained with reference to FIG. 2.

Subsequently, the region specifying unit 36 specifies, using the total contribution degree, a region where sensitivity decreases (step S111).

The sensitivity image generating unit 37 generates data of a sensitivity image based on the total contribution degree (step S112). Specifically, the sensitivity image generating unit 37 generates data of a sensitivity image by, for example, allocating a color corresponding to the total contribution degree to an ultrasound beam correspondence region in an ultrasound image.

Thereafter, the control unit 39 causes the display device 4 to display the sensitivity image (step S113). The display device 4 displays, for example, the sensitivity image 100 illustrated in FIG. 3. In this case, the control unit 39 may cause the display device 4 to display, together with the sensitivity image, a message for informing that the sensitivity decreased element is present or a message for informing a degree of a sensitivity decrease for each of the ultrasound beams. After step S113, the ultrasound imaging device 3 ends a series of processing.

Note that, after step S113, when the input unit 38 receives an input of a signal for instructing erasing of the sensitivity image, the control unit 39 may cause the display device 4 to end the display of the sensitivity image. After a predetermined time has elapsed from a start of the display of the sensitivity image by the display device 4, the control unit 39 may cause the display device 4 to end the display of the sensitivity image.

When the input unit 38 does not receive an input of a start instruction signal in step S103 (step S103: No), the ultrasound imaging device 3 ends a series of processing when a predetermined time has elapsed from a start of display of a start message (step S114: Yes). When the predetermined time has not elapsed in step S114 (step S114: No), the ultrasound imaging device 3 returns to step S103.

According to the first embodiment of the disclosure explained above, the data of the sensitivity image that displays the region where the sensitivity decreases in the ultrasound image is generated based on the contribution degree to the ultrasound beam for the element determined as the sensitivity decreased element having the sensitivity decrease. Therefore, the user is capable of intuitively grasp the influence on the ultrasound image due to the sensitivity decrease of the ultrasound element included in the ultrasound probe.

According to the first embodiment, for example, when local observation is performed, the user can select and use a portion with less influence of a sensitivity decrease.

Second Embodiment

An ultrasound imaging device according to a second embodiment of the disclosure specifies a sensitivity decreased part by performing, for each depth, determination of the sensitivity decreased part and generates data of a sensitivity image. A configuration of an ultrasound diagnosis system according to the second embodiment is the same as the configuration in the first embodiment. In the following explanation, components of the ultrasound diagnosis system are denoted by the same reference numerals and signs as those in the first embodiment.

FIGS. 5 to 7 are diagrams for explaining an overview of processing performed by the sensitivity image generating unit 37 in this second embodiment. In FIGS. 5 to 7, an overview of processing in depth regions D1 to D3 different from one another is illustrated. Specifically, FIG. 5 illustrates an overview of processing in the depth region D1 having the smallest depth. FIG. 7 illustrates an overview of processing in the depth region D3 having the largest depth. Like FIG. 2, FIGS. 5 to 7 illustrate a case in which one ultrasound beam is formed using five elements E1 to E5 and the element E2 and the element E3 among the five elements E1 to E5 are determined as sensitivity decreased elements by the determining unit 35.

An ultrasound beam Bij (i=1 to 5, j=1 to 3) means an ultrasound beam Bi in a depth region Dj. The ultrasound beam Bij has the highest contribution degree of an element Ei, and has a lower contribution degree of an element that is farther from the element Ei. For example, for an ultrasound beam B11, a contribution degree of the element E1 is 75%, a contribution degree of the element E2 is 25%, and contribution degrees of the elements E3 to E5 are respectively 0% (FIG. 5). For an ultrasound beam B12, a contribution degree of the element E1 is 70%, a contribution degree of the element E2 is 20%, a contribution degree of the element E3 is 10%, and contribution degrees of the elements E4 and E5 are respectively 0% (FIG. 6). For an ultrasound beam B13, a contribution degree of the element E1 is 68%, a contribution degree of the element E2 is 18%, a contribution degree of the element E3 is 9%, a contribution degree of the element E4 is 5%, and a contribution degree of the element E5 is 0% (FIG. 7).

For an ultrasound beam B21, a contribution degree of the element E2 is 50%, contribution degrees of the elements E1 and E3 are respectively 25%, and contribution degrees of the elements E4 and E5 are respectively 0% (FIG. 5). For an ultrasound beam B22, contribution degrees of the elements E2 and E3 are respectively 40%, contribution degrees of the elements E1 and E4 are respectively 10%, and a contribution degree of the element E5 is 0% (FIG. 6). For an ultrasound beam B23, in a region where depth is the largest, contribution degrees of the elements E2 and E3 are respectively 38%, contribution degrees of the elements E1 and E4 are respectively 9%, and a contribution degree of the element E5 is 6% (FIG. 7).

Note that setting of the contribution degrees illustrated in FIGS. 5 to 7 are only an example. Division in the depth direction and setting of contribution degrees are not limited to this.

The sensitivity image generating unit 37 calculates, for each of depth regions, a total contribution degree obtained by totaling contribution degrees to each ultrasound beam for sensitivity decreased elements. Total contribution degrees to ultrasound beams Bi1 (i=1 to 5) in a case illustrated in FIG. 5 are respectively the same as the total contribution degrees to the ultrasound beam Bi in FIG. 2. In a case illustrated in FIG. 6, a total contribution degree to an ultrasound beam B12 is 20(%)+10(%)=30(%), a total contribution degree to an ultrasound beam B22 is 40(%)+40(%)=80(%), a total contribution degree to an ultrasound beam B32 is 10(%)+40(%)=50(%), a total contribution degree to an ultrasound beam B42 is 10(%)+40(%)=50(%), and a total contribution degree to an ultrasound beam B52 is 0(%)+10(%)=10(%). In a case illustrated in FIG. 7, a total contribution degree to an ultrasound beam B13 is 18(%)+9(%)=27(%), a total contribution degree to an ultrasound beam B23 is 38(%)+38(%)=76(%), a total contribution degree to an ultrasound beam B33 is 20(%)+38(%)=58(%), a total contribution degree to an ultrasound beam B43 is 9(%)+38(%)=47(%), and a total contribution degree to an ultrasound beam B53 is 5(%+9(%=14(%.

In FIGS. 5 to 7, correspondence between the total contribution degrees and display colors is the same as the correspondence in the first embodiment. That is, when the total contribution degree is 0% or more and less than 25%, “white” is allocated. When the total contribution degree is 25% or more and less than 60%, “yellow” is allocated. When the total contribution degree is 60% or more, “red” is allocated.

The sensitivity image generating unit 37 generates data of a sensitivity image based on the calculated total contribution degree. In this case, the sensitivity image generating unit 37 allocates, for each of depth regions of an ultrasound image generated by the ultrasound beams, a color corresponding to the total contribution degree and generates data of a sensitivity image that displays sensitivity information of the depth region.

Figure 8:
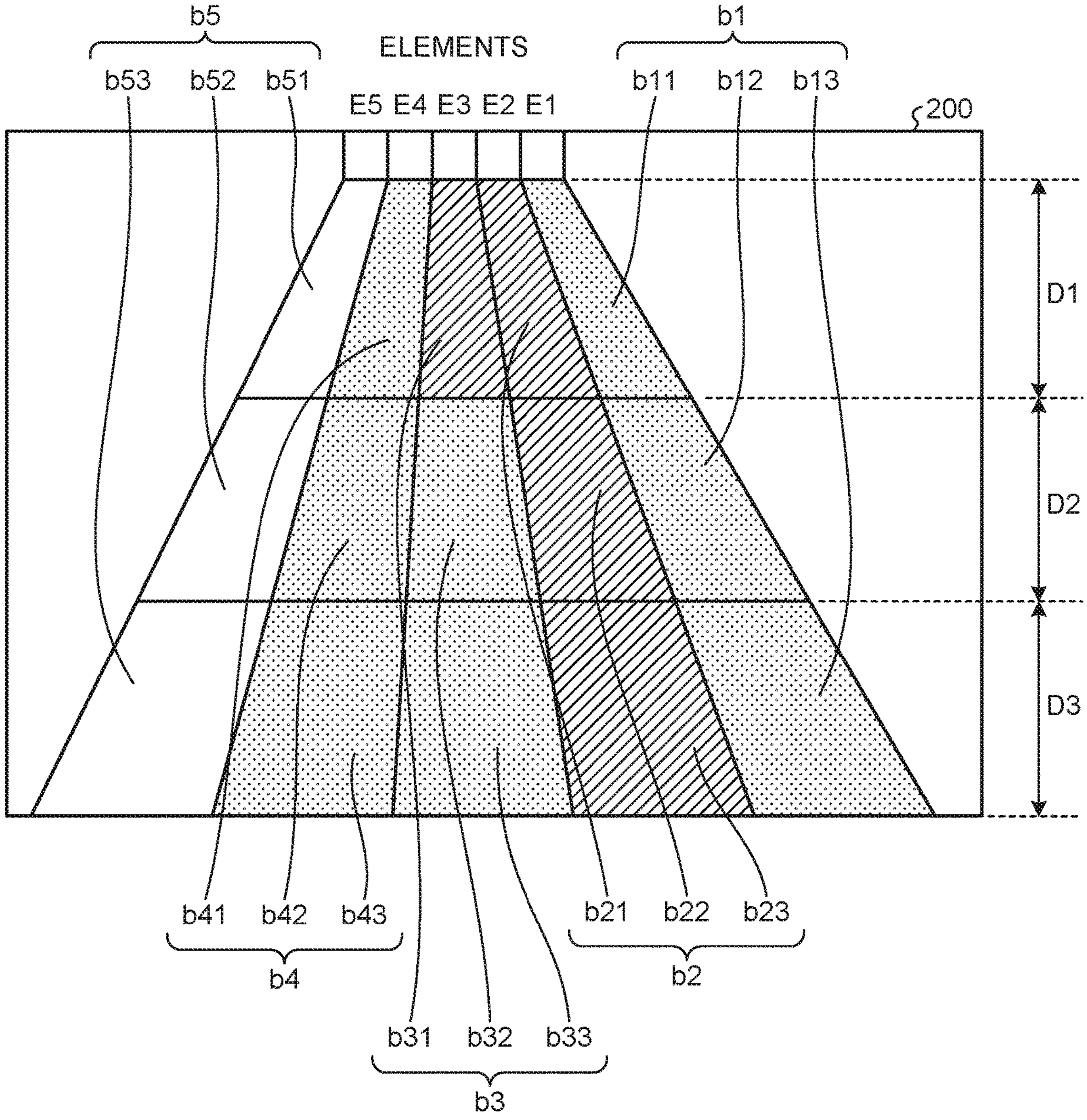
FIG. 8 is a diagram illustrating a display example of a sensitivity image displayed by a display device in the second embodiment of the disclosure.

FIG. 8 is a diagram illustrating a display example of a sensitivity image displayed by the display device 4. In a sensitivity image 200 illustrated in the figure, a display form is decided for each partial beam region bij corresponding to the ultrasound beam Bij. Specifically, the sensitivity image 200 displays, in yellow (in FIG. 8, dots), a beam region b1 (b1, b12, b13) corresponding to an ultrasound beam B1 (B11, B12, B13) and a beam region b4 (b41, b42, b43) corresponding to an ultrasound beam B4 (B41, B42, B43). The sensitivity image 200 displays, in red (in FIG. 8, slanted lines), a beam region b2 (b21, b22, b23) corresponding to an ultrasound beam B2 (B21, B22, B23) and displays, in white, a beam region b5 (b51, b52, b53) corresponding to an ultrasound beam B5 (B51, B52, B53). The sensitivity image 200 displays each of partial beam regions in a different color in a beam region b3 corresponding to an ultrasound beam B3. Specifically, the sensitivity image 200 displays a partial beam region b31 in red (in FIG. 8, slanted lines) and displays partial beam regions b32 and b33 in yellow.

Overview of processing in the second embodiment corresponds to the flowchart of FIG. 4 explained in the first embodiment. However, in step S110, as explained above, the region specifying unit 36 calculates a total contribution degree for each of the depth regions of the ultrasound beam. In step S111, the region specifying unit 36 specifies, for each of depth regions of the ultrasound beam, a region where sensitivity decreases. In step S112, the sensitivity image generating unit 37 generates data of a sensitivity image by allocating a color corresponding to the total contribution degree to each of the depth regions of the ultrasound beam.

According to the second embodiment of the disclosure explained above, as in the first embodiment, a user can intuitively grasp influence on the ultrasound image due to the sensitivity decrease of the ultrasound elements included in the ultrasound probe.

According to the second embodiment, the data of the sensitivity image is generated using a different contribution degree according to depth that ultrasound reaches. Therefore, it is possible to more accurately inform only a sensitivity decreased part in which influence occurs in the ultrasound image.

Other Embodiments

The modes for carrying out the disclosure are explained above. However, the disclosure should not be limited by only the embodiments explained above. For example, instead of calculating the sensitivity values using the RF data, the determining unit 35 may calculate an average of luminance values of the pixels after the RF data is converted into image data by performing the same processing as the processing during the generation of the data of the ultrasound image and use the average as sensitivity information to thereby determine presence or absence of a sensitivity decrease of the elements.

Determination processing for presence or absence of a sensitivity decrease of the elements in the determining unit 35 is not limited to the determination processing explained above. For example, the determining unit 35 may set an element having a sensitivity value smaller than a threshold as a candidate element, calculate a statistical value such as an average, a sum, dispersion, or a mode of sensitivity values of a predetermined number of elements near the candidate element, and determine the candidate element as a sensitivity decreased element when the sensitivity value is smaller than a second threshold decided according to the statistical value. A near field region in this case may be decided according to, for example, a transmission numerical aperture in generating an ultrasound image, may be decided according to a reception numerical aperture different according to depth, or may be decided according to a smaller number of the reception numerical aperture and the transmission numerical aperture for each depth. The near field region may be thinned out and selected at a predetermined interval within a predetermined range centering on the candidate element or may be selected within the predetermined range randomly. The determining unit 35 may irradiate an ultrasound beam and determine a sensitivity decrease for each of sound rays and, when a sensitivity decrease is present, determine an element in the center of the ultrasound beam as a sensitivity decreased element.

The display device 4 may be able to display the sensitivity decreased part while an examination is performed using the ultrasound diagnosis system 1. For example, when the input unit 38 receives an input of a signal for instructing the display of the sensitivity decreased part during the examination, the sensitivity image generating unit 37 specifies a sensitivity decreased element referring to the storing unit 40 and generates data of a sensitivity image according to the display of the ultrasound image. When the ultrasound image is scrolled, the sensitivity image generating unit 37 also changes a display form of the sensitivity image according to the scroll. The control unit 39 causes the display device 4 to display the sensitivity image and the ultrasound image side by side. Note that the control unit 39 may cause the display device 4 to display the sensitivity image to be smaller than the ultrasound image. Thereafter, when the input unit 38 receives an input of a signal for deleting the display of the sensitivity decreased part, the control unit 39 causes the display device 4 to end the display of the sensitivity image.

The ultrasound imaging device may further include a superimposed-image generating unit that generates data of a superimposed image obtained by superimposing the ultrasound image and the sensitivity image. In this case, when the input unit 38 receives a display instruction input for the sensitivity decreased part during the examination, after the sensitivity image generating unit 37 generates data of a sensitivity image as explained above, the superimposed-image generating unit superimposes the data on data of an ultrasound image to generate data of a superimposed image. The superimposed image may color and display the sensitivity decreased part or may increase the transmittance of the sensitivity decreased part and display the sensitivity decreased part semi-transparently.

Since the ultrasound imaging device has a function of displaying the sensitivity decreased part even during the examination, the user can grasp the sensitivity decreased part even during the examination and make use of the sensitivity decreased part in the examination and diagnosis.

As explained above, the ultrasound imaging device, the operating method of the ultrasound imaging device, and the operating program for the ultrasound imaging device are useful for the user to intuitively grasp influence on an ultrasound image due to a sensitivity decrease of the elements included in the ultrasound probe.

According to the disclosure, the user is capable of intuitively grasp influence on the ultrasound image due to the sensitivity decrease of the ultrasound element included in the ultrasound probe.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound imaging system configured to generate data of an ultrasound image based on an echo signal received by each of a plurality of elements included in an ultrasound transducer that transmits and receives ultrasound, the ultrasound imaging system comprising:

a determining circuit configured to determine, by comparing a first value corresponding to an amplitude of the echo signal received by each of the plurality of elements with a threshold, whether each of the plurality of elements has a sensitivity decrease;

a region specifying circuit configured to specify a region where sensitivity decreases in the ultrasound image, based on a contribution degree indicating a ratio of transmission intensity contributing to an ultrasound beam by each element that has been determined as having the sensitivity decrease by the determining circuit; and a sensitivity display circuit configured to generate data for displaying the region specified by the region specifying circuit.

2. The ultrasound imaging system according to claim 1, wherein the sensitivity display circuit is configured to generate data for displaying the region having one or more of a shape and color corresponding to the contribution degree.

3. The ultrasound imaging system according to claim 1, wherein the region specifying circuit is configured to calculate a total contribution degree, and specify the region based on the calculated total contribution degree.

4. The ultrasound imaging system according to claim 3, wherein the sensitivity display circuit is configured to generate the data for displaying the region by superimposing visual information corresponding to the total contribution degree to the region.

5. The ultrasound imaging system according to claim 1, wherein the region specifying circuit is configured to specify, for each depth that the ultrasound reaches, the region based on the contribution degree in each depth.

6. The ultrasound imaging system according to claim 1, wherein the determining circuit is configured to acquire sensitivity information of one or a plurality of elements, and determine, based on the sensitivity information, whether each element has the sensitivity decrease.

7. The ultrasound imaging system according to claim 1, wherein the determining circuit is configured to perform the determination when it is detected that an ultrasound probe is connected to the ultrasound imaging system.

8. The ultrasound imaging system according to claim 1, wherein the determining circuit is configured to determine, using a sensitivity value that is data of a digital signal calculated from the amplitude as the first value, whether each of the plurality of elements has the sensitivity decrease.

9. The ultrasound imaging system according to claim 1, wherein the determining circuit is configured to determine, by using luminance values of pixels as sensitivity information in the image data of the ultrasound image generated from the signal, whether each of the plurality of elements has the sensitivity decrease.

10. The ultrasound imaging system according to claim 8, wherein the determining circuit is configured to compare the sensitivity value of a candidate element that is an element whose sensitivity value is smaller than a second threshold with a value calculated from sensitivity values of a predetermined number of elements disposed around the candidate element, and determine whether each of the plurality of elements has the sensitivity decrease.

11. An operating method of an ultrasound imaging system configured to generate data of an ultrasound image based on an echo signal received by each of a plurality of elements included in an ultrasound transducer that transmits and receives ultrasound, the operating method of the ultrasound imaging system, comprising:

determining, by comparing a first value corresponding to an amplitude of the echo signal received by each of the plurality of elements with a first threshold, whether each of the elements plurality of has a sensitivity decrease;

specifying a region where sensitivity decreases in the ultrasound image, based on a contribution degree indicating a ratio of transmission intensity contributing to an ultrasound beam by each element that has been determined as having the sensitivity decrease by the determining; and generating data for displaying the region specified in the specifying.

12. The ultrasound imaging system according to claim 1, wherein the determining circuit is configured to determine an element of the plurality of elements as having the first value smaller than the threshold as an element having the sensitivity decrease when the first value is smaller than the first threshold.

13. A non-transitory computer-readable recording medium with an executable program stored thereon, the program causing an ultrasound imaging system configured to generate data of an ultrasound image based on an echo signal received by each of a plurality of elements included in an ultrasound transducer that transmits and receives ultrasound, to execute: determining, by comparing a first value corresponding to an amplitude of the echo signal received by each of the plurality of elements with a first threshold, whether each of the plurality of elements has a sensitivity decrease; specifying a region where sensitivity decreases in the ultrasound image, based on a contribution degree indicating a ratio of transmission intensity contributing to an ultrasound beam by each element that has been determined as having the sensitivity decrease by the determining; and generating data for displaying the region specified in the specifying.

* * * * *